United States Patent [19]

Gussman et al.

[11] Patent Number: 5,174,163
[45] Date of Patent: Dec. 29, 1992

[54] GAS SAMPLING APPARATUS

[75] Inventors: Robert A. Gussman; Gertrude A. Gussman; Kevin E. DeVoe, all of Waltham, Mass.

[73] Assignee: BGI Incorporated, Waltham, Mass.

[21] Appl. No.: 643,042

[22] Filed: Jan. 18, 1991

[51] Int. Cl.⁵ .............................................. G01N 1/14
[52] U.S. Cl. .................................. 73/864.62; 251/352
[58] Field of Search .................... 73/863.86, 864.62; 251/144, 352, 48

[56] References Cited

U.S. PATENT DOCUMENTS

| | | | |
|---|---|---|---|
| 3,319,927 | 5/1967 | Thompson | 251/352 |
| 3,877,676 | 4/1975 | Forchini et al. | 251/145 |
| 4,209,115 | 6/1980 | Stahl | 251/352 |
| 4,240,523 | 12/1980 | Nestor et al. | 251/98 |
| 4,542,763 | 9/1985 | Gardner et al. | 251/305 |
| 4,850,540 | 7/1989 | Taniguchi | 251/352 |
| 4,974,813 | 12/1990 | Hannon, Jr. | 251/352 |
| 4,989,791 | 2/1991 | Ridenour | 251/352 |

FOREIGN PATENT DOCUMENTS 0568863 8/1977 U.S.S.R. .......................... 73/864.62

Primary Examiner—Robert Raevis
Attorney, Agent, or Firm—Schiller & Kusmer

[57] ABSTRACT

A gas sampling apparatus including a flexible, substantially gas-impervious, closed bag and a valve assembly mounted in a wall of the bag for providing control of gas flow between the interior and exterior of the bag. The valve assembly includes a valve body mounted in the bag wall for providing a first gas conduit to and from said interior of the bag, and a valve stem for providing a second gas conduit, the stem terminating at one end in a ball mounted on the valve body. The stem is movable about the ball between an opened position in which the gas conduits are in communication with one another and the bag may be filled or emptied through the coupled conduits, and a closed position in which the ball seals the first conduit. A valve cap is provided for capturing the stem at variable pressures between the valve body and the cap. The cap has a slot in one side in which the stem is movable tranversely to its long axis between its opened and closed positions. The stem includes a pair of radially projecting lugs positioned so that when the stem is in its closed position, the stem can be rotated about its long axis to lock the lugs against the edges of the slot.

11 Claims, 2 Drawing Sheets

GAS SAMPLING APPARATUS

This invention relates to gas sampling apparatus, and more particularly to a flexible container specially adapted for gas sampling.

Flexible containers such as bags have been used to capture and transport intact samples of gases to an analytical site, particularly for atmospheric diffusion studies. The reasons mandating use of such bags are U.S. government regulations (NIOSH/EPA), low cost, simplicity and reliability. Typically, such bags are made of polymeric material selected according to several criteria such as cost, strength, abrasion resistance, permeability and absorptivity for the gases being sampled, storage time prior to analysis and storage temperature. The principal materials currently used for such bags are polytetrafluorethylene, polyvinylfluoride and multilayer composites of metal foil and plastic.

The sampling bag is provided with a valve to permit loading and unloading, the valve when closed serving to seal the bag. Obviously too, the bag and valve arrangement should not leak to the environment when being filled or emptied. Such valves are made of substances that are non-reactive with the gases of interest, typically being formed of stainless steel, polytetrafluorethylene and the like.

In addition to the valve, the sampling apparatus is usually provided with a septum for extracting an aliquot of the sample through a syringe and needle. Such septa typically are formed of a thin layer of polytetrafluorethylene bonded to a thicker layer of a material, such as silicone rubber, that will heal after a needle puncture.

The bag assembly is essentially non-reusable, having been contaminated by the sample, hence current practise is to discard used bags. It is not practical to remove and reuse the stainless steel valves although the cost of manufacture of such valves has heretofore been a relatively large part of the cost of the bag assembly.

A principal object of the present invention is therefore to provide a gas-sampling bag assembly which includes a valve mounted in a wall of the bag, which valve is being formed of a minimal number of parts, can be made relatively inexpensively and can be discarded with small cost. Further objects of the present invention are to provide such a valve that is easy to operate, to provide such a valve that will provide positive closure and access into the interior of the bag, to provide such a valve that can be locked in its shut or closed position, and to provide means for mounting the valve in the wall of the bag so as to minimize abrasion of the bag wall by the valve body.

These and other objects are achieved by providing a gas sampling apparatus that includes a flexible, substantially gas-impervious, closed bag and a valve assembly mounted in a wall of the bag for providing control of gas flow between the interior and exterior of the bag. The valve assembly includes a valve body mounted in the bag wall for providing a first gas conduit to and from said interior of the bag, and a valve stem for providing a second gas conduit, the stem terminating at one end in a rounded body such as a ball mounted on the valve body. The stem is movable about the ball between an opened position in which the gas conduits are in communication with one another and the bag may be filled or emptied through the coupled conduits, and a closed position in which the ball seals the first conduit. Means, such as a valve cap, is provided for capturing the stem at variable pressures between the valve body and the cap. The cap has a slot in one side in which the stem is movable tranversely to its long axis about the ball between its opened and closed positions. The stem includes a pair of radial projections such as pins or lugs positioned so that when the stem is in its closed position, the stem can be rotated about its long axis to lock the lugs against the edges of the slot.

Other objects of the invention will in part be obvious and will in part appear hereinafter. The invention accordingly comprises the apparatus possessing the construction, combination of elements, and arrangement of parts which are exemplified in the following detailed disclosure, and the scope of the application of which will be indicated in the claims.

For a fuller understanding of the nature and objects of the present invention, reference should be made to the following detailed description taken in connection with the accompanying drawings wherein.

Figure 1:
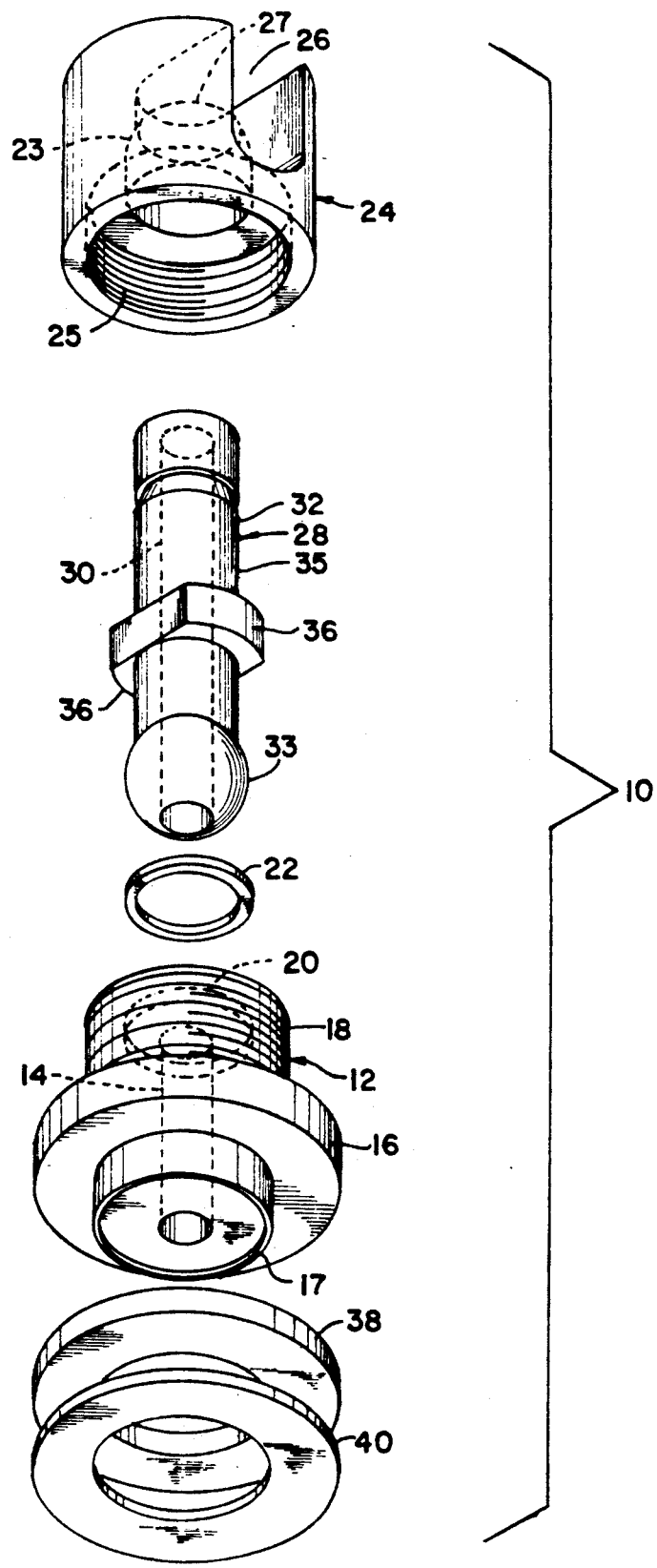
FIG. 1 is an exploded isometric view of the parts of the valve of the present invention, interior portions being shown in dotted lines.

The present invention includes valve 10 that is intended to be coupled through one wall of a container such as a bag as hereinafter described. As shown in FIG. 1, valve 10 includes valve body 12 having a central gas conduit or bore 14. Valve body 12 is provided adjacent one end thereof with thick, circular flange 16 from which thin, concentric ring 17, of lesser diameter than flange 16, depends, to form one end of valve body 12. The opposite end of the valve body is formed as an externally threaded neck 18 surrounding bore 14 and extending upwardly from flange 16. The upper end of neck 18 is provided with a depression such as well 20 in which an elastomeric O-ring 22 can be disposed around central bore 14. Valve body 12 is preferably made of a metal that is subtantially non-reactive chemically with either the gases being sampled or the material of the bag.

Valve cap 24 has a substantially hollow interior 23, preferably semi-globular or hemispherical, the equitorial plane of which opens into or is coupled to cylindrical conduit 25 of like diameter, conduit 25 extending through one end of cap 24. Conduit 25 is internally threaded and has a diameter selected so that it can be screwed onto threaded neck 18. The top curved surface of hollow interior 23 is connected to or opens into slot 26 that extends both radially across and longitudinally through much of the length of cap 24, slot 26 having a portion 27 thereof that is coaxial with conduit 25 and extends toward the oppposite end of cap 24.

Valve 10 also includes elongated valve stem 28 having central gas conduit 30 extending axially throughout its length. Stem 28 is formed as a substantially cylindrical body 32 connected at one end to ball portion 33. The upper end of conduit 30 disposed within body 32 is slightly tapered to accept a Luer-type syringe neck. Ball portion 33 is dimensioned with substantial clearance so as to fit loosely within interior 23 of valve cap 24 when stem 28 is inserted into conduit 25 upon assembly. Intermediate portion 35 of stem 28 is provided with a pair of locking lugs 36 that extend outwardly transversely to the long axis of valve stem 28. The side edges of lugs 36 extend flush with the outer cylindrical surface of stem 28.

As means for sealing valve 10 into one wall of a container, the valve is provided with a pair of washers, dimensioned to fit around the periphery of ring 17, one washer 38 being preferably formed of an elastomeric material and being adapted to contact the lower flat surface of flange 16. The other washer 40 is preferably formed as a very thin metallic ring of the same radial dimensions as washer 38.

Figure 2:
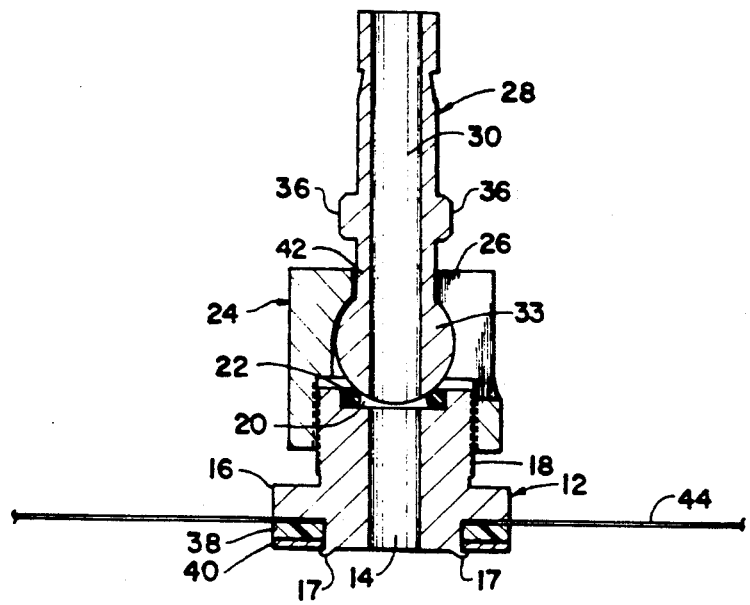
FIG. 2 is a sectional side elevational view of the elements of the present invention in assembled form with the valve in an open position.
Figure 3:
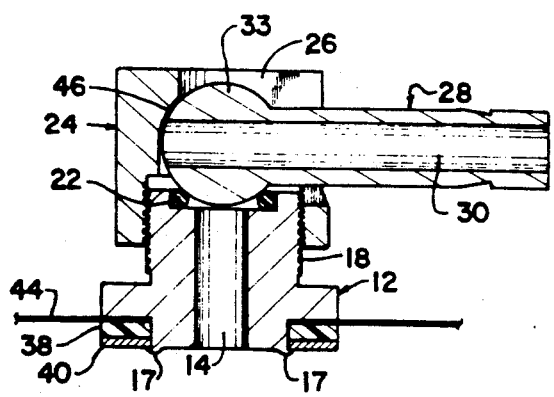
FIG. 3 shows the elements of FIG. 2 with the valve in a closed position.

As shown particularly in FIGS. 2 and 3, the parts thus described are easily assembled by inserting length 42 of stem 28 into conduit 25 until ball portion 33 seats loosely in hemispherical hollow interior 23, lugs 36 being positioned so that at least one thereof slides along slot 26. O-ring 22 is then seated in well 20, and threaded neck 18 of valve body 12 is engaged with the threaded interior of conduit 25. Rotation of the valve body relative to cap 24 in an appropriate direction will then capture ball portion 33 between well 20 and interior 23.

The valve assembly thus made is coupled, as shown in FIG. 2 in fragment, to one wall 44 of a plastic bag through a hole in the latter, the edges of the hole being captured between flange 16 and elastomeric washer 38 inasmuch as the hole in wall 44 must be smaller than the diameter of the flange. The elastomeric washer is held under compression in place by thin metal washer 40, the periphery of which is locked against washer 38 by swaging the outer edges of ring 17 down onto washer 40 particularly as shown in FIGS. 2 and 3.

In operation, valve 10 is open, as shown in FIG. 2, when the valve stem is in an upright position in which central conduit 30 in the valve stem communicates directly with conduit 14 in valve body 12. The valve stem can only be moved out of this upright position when the pressure on ball 33 by cap 24 does not lock ball 33 against O-ring 22. Of course, that pressure is adjustable by rotating cap 24 relative to valve body 12. Valve stem 28 is moved into a horizontal position (i.e., substantially normal to the upright position with respect to the valve body) by aligning lugs 36 with slot 26 and moving valve stem 28 in an arc in its axial plane downwardly into slot 26. Once valve stem 28 is in the horizontal position as shown in FIG. 3, if cap 24 is rotated to increase the compression against ball 33, the latter locks against O-ring 22, effectively sealing conduit 14. If gas is introduced now into the upper end of valve stem 28, because of the clearance between interior 23 and ball 33 due to the mismatch in diameters, a bleed to interspace 46 is provided, permitting one to purge all of the lines leading to valve stem 28 and fill conduit 30 with the gas of interest. If now the valve stem is again rotated to its vertical position, that gas can be introduced into the sampling bag.

Figure 4:
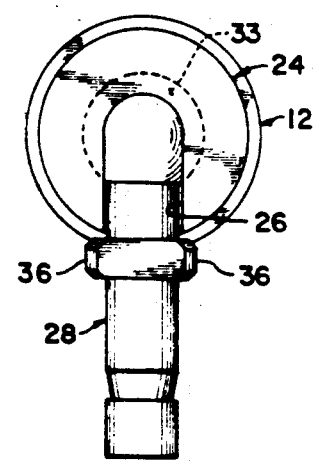
FIG. 4 is a top view of assembled parts of the present invention showing the valve stem locked to the valve body thereof.

Once a sufficient sample has been taken, valve stem 28 can again be brought to a horizontal position closing the valve. If one now rotates valve cap 24 to increase the compression against ball 33, a tight gas seal is effected. If one wishes to lock the valve stem in a horizontal position, prior to immobilizing the ball by increasing the compression by rotating cap 24, one need only rotate the valve stem around its long axis so that the projecting ends of lugs 36 are rotated 90 degrees to extend beyond the width of slot 26. The valve stem can now no longer be moved to a vertical position because the lugs will engage the outer edges of slot 26 as shown in FIG. 4.

For accurate testing, the valve stem and valve body are made of stainless steel, but because the cap never contacts the gas that is placed into the bag, the cap can be made of aluminum, plastic or other solid material.

Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. Gas sampling apparatus, comprising, in combination:
    a substantially gas-impervious, closed, flexible container; and
    a valve assembly mounted in a wall of said container for providing control of gas flow between the interior and exterior of said container, said valve assembly including:
    a valve body sealed into said wall for providing a first gas conduit to and from said interior of said chamber;
    an elongated valve stem for providing a second gas conduit and being coupled to said valve body for movement along an arc transversely to the axis of elongation of said valve stem between an open position wherein said gas conduits are in communication with one another, and a closed position wherein at least a portion of said stem provides a seal for said first conduit; and
    releasable, positive locking means for locking said stem in said closed position by rotation of said valve stem in one direction around said axis of elongation to a locked position wherein said stem cannot be moved along said arc, and for unlocking said stem from said locked position by rotation of said stem about said axis of elongation in the opposite direction to an unlocked position.

2. Gas sampling apparatus as defined in claim 1 including an aperture in said wall of said container; and
    including means for sealing said valve assembly into said wall, said means for sealing comprising;
    a metallic circular flange forming one end of said valve body and dimensioned to be larger than the maximum dimension of said aperture, an opening in said flange forming one end of said first conduit, said flange including a thin metallic ring projecting therefrom and surrounding said opening; one surface of said wall of said container being disposed against said flange with said aperture substantially registered with said opening; and
    means disposed about said aperture for holding said wall in compression against said flange and being locked against said wall by edge portions of said ring.

3. Gas sampling apparatus as defined in claim 2 wherein said means disposed about said aperture comprises:
    an elastomeric washer having one side thereof disposed against the other surface of said wall and surrounding said aperture; and
    a metallic washer mounted on the other side of said elastomeric washer surrounding said aperture, at least an edge portion of said ring being swaged onto said metallic washer to hold the latter, said elastomeric washer and said wall in a compression seal.

4. Gas sampling apparatus as defined in claim 1 wherein said first gas conduit terminates at respective openings in opposite ends of said valve body, said apparatus including means for sealing one end of said valve body into said wall of said container so that a first of said openings communicates with the interior of said container, the second of said openings being surrounded by a depression in said valve body, said valve stem being coupled to said valve body at said depression.

5. Gas sampling apparatus as defined in claim 4 wherein said valve stem is an elongated body having a substantially cylindrical portion joined to a ball portion, said second conduit extending inside said stem between opposite ends of said stem, said ball portion being disposed adjacent said depression in said valve body, said apparatus further including an O-ring disposed in said depression and surrounding said first of said openings in said valve body.

6. Gas sampling apparatus as defined in claim 5 including a hollow valve cap mounted on said valve body and surrounding said stem for holding said ball portion of said stem against said O-ring, said valve cap having a slot therein extending along at least one side thereof, said stem being movable transversely to the long axis thereof about said ball portion along said slot between said open and closed positions.

7. Gas sampling apparatus as defined in claim 6 wherein said valve stem is rotatable about said ball portion around said long axis and said locking means includes at least one protrusion so mounted on said cylindrical portion of said stem and spaced from said ball portion that when said stem is in said closed position, rotation of said stem around said long axis will bring said protrusion into such contact with an edge of said slot as to prevent motion of said stem transversely to said long axis.

8. Gas sampling apparatus as defined in claim 7 wherein said valve cap is threadingly mounted on said valve body so that rotation of said valve cap relative to said valve body in a first direction will cause said ball portion of said valve stem to be so forced by said valve cap against said O-ring as to prevent motion of said valve stem both transversely and around said long axis.

9. Gas sampling apparatus as defined in claim 6 wherein said hollow interior in said valve cap surrounding said ball portion is substantially greater in diameter so as to provide a bleed space for gas traversing said second gas conduit when said stem is in said closed position.

10. Gas sampling apparatus as defined in claim 6 wherein said valve stem is rotatable about said ball portion around said long axis and said locking means includes a pair of protrusions mounted in diametrially opposed positions on said cylindrical portion of said stem, the width of said protrusions being less than the width of said slot, said protrusions being spaced from said ball portion such that when said stem is in said closed position, rotation of said stem around said long axis will bring said protrusions into such contact with respective edges of said slot as to prevent motion of said stem transversely to said long axis.

11. A valve assembly for providing control of fluid flow between the interior and exterior of a closed chamber, said valve assembly comprising, in combination:

a valve body adapted to be sealably emplaced in a wall of said chamber for providing a first gas conduit to and from said interior of said chamber;

an elongated valve stem for providing a second gas conduit and being coupled to said valve body for movement along an arc transversely to the axis of elongation of said valve stem between an open position wherein said gas conduits are in communication with one another, and a closed position wherein at least a portion of said stem provides a seal for said first conduit; and releasable, positive locking means for locking said stem in said closed position by rotation of said valve stem in one direction around said axis of elongation to a locked position wherein said stem cannot be moved along said arc, and for unlocking said stem from said locked position by rotation of said stem about said axis of elongation in the opposite direction to an unlocked position.

* * * * *